(12) United States Patent
Vestevich

(10) Patent No.: US 9,332,954 B2
(45) Date of Patent: May 10, 2016

(54) SYSTEMS AND METHODS FOR EVALUATING A BRAIN SCAN

(71) Applicant: Jacqueline K. Vestevich, Chicago, IL (US)

(72) Inventor: Jacqueline K. Vestevich, Chicago, IL (US)

(*) Notice: Subject to any disclaimer, the term of this patent is extended or adjusted under 35 U.S.C. 154(b) by 135 days.

(21) Appl. No.: 14/217,274

(22) Filed: Mar. 17, 2014

(65) Prior Publication Data

US 2014/0270052 A1 Sep. 18, 2014

Related U.S. Application Data

(60) Provisional application No. 61/798,445, filed on Mar. 15, 2013.

(51) Int. Cl.
*A61B 6/03* (2006.01)
*A61B 6/00* (2006.01)

(52) U.S. Cl.
CPC .......... *A61B 6/5217* (2013.01); *A61B 6/4241* (2013.01); *A61B 6/482* (2013.01); *A61B 6/501* (2013.01); *A61B 6/032* (2013.01)

(58) Field of Classification Search
CPC .......... A61B 6/03; A61B 6/032; A61B 6/482; A61B 6/501; A61B 6/5217; G06T 7/0014
USPC .......... 378/4, 5, 38–40, 62, 16, 98.9, 98.11; 382/131
See application file for complete search history.

(56) References Cited

U.S. PATENT DOCUMENTS

| | | | | |
|---|---|---|---|---|
| 7,611,281 B2 * | 11/2009 | Sukovic | ............... | A61B 6/035 378/197 |
| 8,157,742 B2 * | 4/2012 | Taylor | ............... | A61B 5/02007 600/481 |
| 8,199,982 B2 * | 6/2012 | Fueyo | ............... | A61B 6/037 382/128 |
| 8,437,523 B2 * | 5/2013 | Shuke | ............... | A61B 6/501 378/21 |
| 8,467,585 B2 * | 6/2013 | Rao | ............... | G06T 7/0012 128/922 |
| 8,488,857 B2 * | 7/2013 | Young | ............... | A61B 6/5247 362/209 |
| 8,492,107 B2 * | 7/2013 | Wang | ............... | C07K 16/18 435/4 |
| 8,509,507 B2 * | 8/2013 | Meetz | ............... | G06T 7/0012 128/922 |
| 8,676,294 B2 * | 3/2014 | Kakimoto | ............... | G06F 19/345 600/407 |
| 8,693,746 B2 * | 4/2014 | Ishii | ............... | A61B 6/032 382/128 |
| 8,774,481 B2 * | 7/2014 | Schreibmann | ............... | G06T 7/0024 378/4 |
| 9,042,616 B2 * | 5/2015 | Goto | ............... | A61B 5/055 378/4 |

* cited by examiner

*Primary Examiner* — Allen C. Ho
(74) *Attorney, Agent, or Firm* — Richards Patent Law P.C.

(57) ABSTRACT

The present disclosure provides systems and methods for evaluating a brain scan using reference data. Specifically, the systems and methods include a computed tomography (CT) scanner for the purpose of diagnosing concussions or mild traumatic brain injuries (mTBI). The system includes a multi-energy x-ray source (i.e., spectral CT), a photon counting x-ray detector, and a content-aware computer aided diagnostic (CAD) algorithm designed to detect imperceptible changes indicative of structural and physiological damage caused by a concussive event by comparing raw volumetric datasets of baseline (healthy) reference scan data to patient scan data taken after a concussive event.

16 Claims, 2 Drawing Sheets

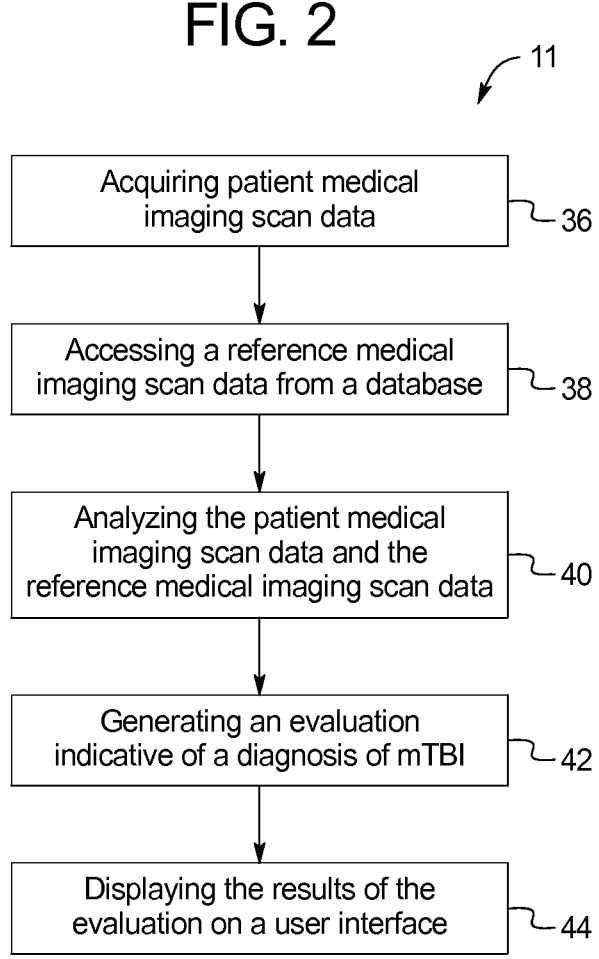

SYSTEMS AND METHODS FOR EVALUATING A BRAIN SCAN

CROSS-REFERENCE TO RELATED APPLICATIONS

This application incorporates by reference and claims priority to U.S. Provisional Application 61/798,445 filed on Mar. 15, 2013.

BACKGROUND OF THE INVENTION

The present subject matter relates generally to systems and methods for evaluating a brain scan. More specifically, the present invention relates to objective systems and methods for evaluating a brain scan using reference data to detect acute injury, such as a concussion, or detecting chronic injury such as chronic traumatic encephalopathy.

Brain injury, such as a concussion, can cause physiological and psychological problems, and even disability or death. Repeated brain injury, an unfortunately common occurrence in professional athletics, such as football or boxing, may cause serious conditions later in life, such as chronic traumatic encephalopathy. However, the lack of the highly noticeable external signs and symptoms cause clinicians to fail to identify brain injuries caused by head trauma. Further, it is known that athletes may minimize their symptoms to remain in competition. Thus, there is a need to detect brain injury caused by head trauma, particularly at the location the injury occurs, such as on the sidelines or in the locker room at a sporting event.

Previous attempts to detect injury to the brain have used non-invasive techniques such as CT scans, MRI, etc. that produce scans read by a physician. These scan techniques rely on the ability to detect structural damage from visual inspection of scan images. But, in the case of mild injury, such as that associated with concussions, the physiological or anatomical changes may not be present in scan images or may be faint. Further, detection of injury by physicians from visual inspection of scan images may be unreliable due to the skill level of the physician or subjective interpretation of the faint injury in the scan images. Moreover, these tests and devices require dedicated facilities and are not readily available at the point of injury.

Currently there is no practical objective method of diagnosing concussions. The visual output provided by conventional models of diagnostic medical imaging, such as computed tomography (CT) and magnetic resonance imaging (MRI), are not sensitive enough to detect the subtle brain injuries incurred in concussive events. And while newer neuroimaging technologies and histological testing techniques have proven successful in detecting biomarkers for concussion, none is practically suited for immediate, on-site diagnosis of concussions at sporting events.

Presently, sideline healthcare providers administer a series of tests to evaluate a patient's subjective responses to twenty-four questions about symptoms, which are presumed to be a diagnostic of concussion. Thereafter, the patient is simply observed over time to see whether these subjective symptoms manifested themselves in the patient. Recent advancements in identifying diagnostic biomarkers for mild traumatic brain injury (mTBI) are limited to expensive and invasive tests that are impractical for timely on-site diagnostic testing and post-injury periodic follow up tests, including highly specialized magnetic resonance (MR) techniques, positron emission tomography (PET) scans and laboratory tests of brain tissue, cerebral spinal fluid (CSF), blood serum, and cell cultures.

The lack of an objective diagnostic tool to confirm or rule out a concussion leads to unnecessary delays in diagnosis and treatment during a vital time period, the "Golden Hour" (the first hour after a concussive injury occurred), which can allow an untreated concussive injury to worsen. The lack of a definitive diagnosis also impacts a coaching staff's decision as whether to return a potentially injured athlete to a game or practice, leaving the injured person exposed to the very circumstances that might aggravate his existing injuries.

Traditional markers of mTBI include loss of consciousness, post-traumatic amnesia, Glasgow coma scale, (day of injury) conventional CT, and post-concussion syndrome are either indirect or inconclusive of neuropathological injury caused by mTBI. It is known that Biomarkers may be used to identify mTBI, but the newest means of detecting biomarkers of mTBI, such as specialized neuroimaging technologies and techniques and cell culture and blood and cerebral spinal fluid (CSF) analyses, are expensive, time-consuming, and highly invasive.

What is needed is one or more scan evaluation techniques that enable the detection of brain injuries that are not readily apparent from visual inspection of the scan data. Further what is needed is scan evaluation techniques that are objective and do not rely on the skill level of the physician or a subjective interpretation of the scan images.

Accordingly, there is a need for objective systems and methods for evaluating a brain scan using reference data, as described herein.

BRIEF SUMMARY OF THE INVENTION

To meet the needs described above and others, the present disclosure provides objective systems and methods for evaluating a brain scan using reference data. Specifically, the systems and methods use the dataset provided from a medical imagining device (e.g., computed tomography (CT), magnetic resonance imaging (MRI), etc.) to derive an objective diagnosis of concussions or mild traumatic brain injuries (mTBI). The present subject matter is not specifically intended to visually display images that show the existence of an mTBI, but rather to use the data collected by a medial imaging device to identify the existence of an mTBI. Although a portable CT scanner is the medical imaging device primarily used throughout the present disclosure to explain the features and functions of the systems and methods provided herein, it is understood that one or more other medical imaging devices, such as, for example, an MRI device, an ultrasound device, a positron emission tomography (PET) scanner, etc. may be used in combination with or in substitution for the CT scanner used in the examples below.

In one example, the systems and methods include a CT scanner for the purpose of diagnosing concussions or mTBI. The system includes a multi-energy x-ray source (i.e., spectral CT), a photon counting x-ray detector, and a content-aware computer aided diagnostic (CAD) algorithm designed to detect changes indicative of structural and physiological damage caused by a concussive event that may be visually imperceptible in a tomographic image, or the three-dimensional image formed by a series of tomographic images, by comparing raw volumetric datasets of baseline (healthy) reference scan data to patient scan data taken after a concussive event.

The multi-energy energy x-ray source identifies and quantifies on an absolute and relative basis the anatomical constituents of the brain and cranium. The photon-counting x-ray detector maximizes the accuracy of tissue identification and minimizes radiation dose through a single scan. A content-aware computer aided diagnostic focuses on detecting pre-set mTBI biomarkers in specific regions of interest (ROI) where physical evidence of mTBIs have previously been proven to occur. The computer aided diagnostic may include a subtraction algorithm that compares and contrasts raw volumetric CT datasets (sinograms) between baseline (healthy) reference scan data and post-concussive injury patient scan data, automatically registering and removing the matching (unchanged) data points and highlighting the outlier data points representing biomarkers of concussive-related changes.

In addition to detecting targeted focal injury, the system compares CT scans to detect *diffuse* injuries following mTBI. The objectively measurable physical changes detected with the system can be used as biomarkers of the structural and physiological damage caused by mTBI, and can be quantified and correlated with regions and neural systems that can explain neuro-behavioral and neuro-cognitive symptoms following a concussive injury. The identified biomarkers with correlating neuropsychology symptoms can serve as objective criteria for diagnosing a concussion.

The system is intended to enable healthcare providers to use a compact, portable CT scanner, along with a standardized neuropsychology symptom checker to immediately diagnose, at the point of injury, a concussion, so that treatment can be immediately begun, and so that the injured person can be removed from circumstances that might result in further or aggravated concussion-related injuries.

The method may include re-scanning the patient in automatically detected regions of interest at certain time intervals following the initial head CT to track physical changes in the brain, which themselves serve as objective diagnostic evidence of the physical injury.

In an embodiment, the computed tomography system includes a multi-energy x-ray source in connection with a photon counting detector configured to collect a patient scan data of a patient. The system also includes a controller and a memory coupled to the controller, wherein the memory is configured to store program instructions executable by the controller. In response to executing the program instructions, the controller is configured to access the patient scan data from the photon-counting detector. The controller is also configured to access a reference scan data associated with the patient from a database in communication with the controller, wherein the database includes a plurality of reference scan data associated with a plurality of patients. The controller is configured to analyze the patient scan data and the reference scan data using a computer aided diagnostic and generate an evaluation based on the analysis, wherein the evaluation identifies biomarkers indicating a mild traumatic brain injury. The controller may be configured to display the evaluation on a user interface.

In an example, the computer-aided diagnostic includes a three-dimensional subtraction between the patient scan data and the reference scan data to identify differences to indicate biomarkers.

The biomarker may be selected from the group consisting of blood vessel build-up around a tau protein tangle, bleeding within the corpus callosum, bleeding within the cerebral cortex, stretching of brain tissue, tearing of brain tissue, compression of brain tissue, tearing of blood vessels, change in ventricle size, and change in brain fluid levels. Alternatively, or in addition to, the biomarker may be selected from the group consisting of atrophy of frontal cortex, atrophy of temporal cortex, atrophy of the medial temporal lobe, shifting of intracranial structures, intracranial hematomas, brain hemorrhages, lesions, contusions, cerebral edema. Alternatively, or in addition to, may be selected from the group consisting of tissue density, changes in blood flow, ischemia, change in fluid levels, absence of tissue, osmotic pressure, hypotension, tau deposition, immunoreactive deposits, neuronal loss, and sub-visual fractures in the cranium. Alternatively, or in addition to, may be selected from the group consisting of: hypointensity burden (HIB) in white matter (WM); vascular pathology; microhemorrhages; hemosiderin in WM; microstructural changes in WM; focal WM loss; whole brain WM loss; focal gray matter (GM) loss; whole brain GM loss; deviation in WM spatial statistics (tract-based spacial statistics or TBSS); edema/neuro-inflammation; tissue hyperintensities in WM and corpus callosum; increase in S100B (s100 calcium binding protein Beta); increase in Cho (Choline) in posterior cingulate gyms; increase in MI (myo-inositol); decrease in NAA (N-acetyl Aspartate) in WM: prefrontal and motor (M1) cortices; increase in glutamate/glutamine (Glx) in WM: posterior cingulate gyms; decrease in Glx in GM; presence of lactate; lipids that are "MR visible"; hypoperfusion (decreased regional cerebral blood flow or rCBF) in cortex; hypoperfusion in frontal and bilateral parietal lobes; hypoperfusion in whole brain, pre-frontal poles, temporal poles, occipital lobes, anterior cingulate gyms cerebellum, posterior cingulate gyms, and hippocampus; WM macrophages; proteins ezrin and moesin ejected from cells into intracellular space; increase in pNFH; increase in tau protein in GM; increase in tau protein in cerebral cortex; abnormal presence of antibodies; abnormal WM; and enlargement of cerebral ventricles.

It is further understood that the systems and methods provided herein will enable those skilled in the art to define and identify further biomarkers not presently defined and identified.

In an embodiment, the method of identifying mild traumatic brain injuries includes acquiring patient scan data of a patient from a multi-energy x-ray source in connection with a photon counting detector, accessing a reference scan data associated with the patient from a database storing a plurality of reference scan data, and analyzing the patient scan data and the reference scan data using a computer aided diagnostic. The method also includes generating an evaluation based on the analysis, wherein the evaluation identifies biomarkers indicating a mild traumatic brain injury, and displaying the evaluation on a user interface.

In an example, the method includes acquiring a first patient scan data at a first time and a second patient scan data at a second time, wherein the first patient scan data is stored in the database as the reference scan data. In yet another example, the analysis includes a three-dimensional subtraction between the patient scan data and the reference scan data to identify differences to indicate biomarkers.

An object of the invention is to objectively detect physiological or anatomical changes to the brain in living persons immediately after head trauma.

Another object of the invention is to objectively evaluate physiological or anatomical changes to the brain in living persons after a period of time post head trauma.

Another object of the invention is to leverage the vast quantity of data available from medical imaging devices that would otherwise get lost in visual representations of the data to trigger an objective diagnosis of mTBI.

An advantage of the invention is that it provides a solution to subjective or faulty interpretation of scans during evaluation and diagnosis.

Another advantage of the invention is that it provides a superior and objective evaluation of brain scan data.

Yet another advantage is that the system is capable of detecting and quantifying plaque and tau proteins, biomarkers for chronic traumatic encephalopathy (CTE), linked to concussions.

It should be noted that various changes and modifications to the presently preferred embodiments described herein will be apparent to those skilled in the art. Such changes and modifications may be made without departing from the spirit and scope of the present invention and without diminishing its attendant advantages.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 2 is a schematic of an embodiment of the system disclosed herein.

DETAILED DESCRIPTION OF THE INVENTION

Figure 1:
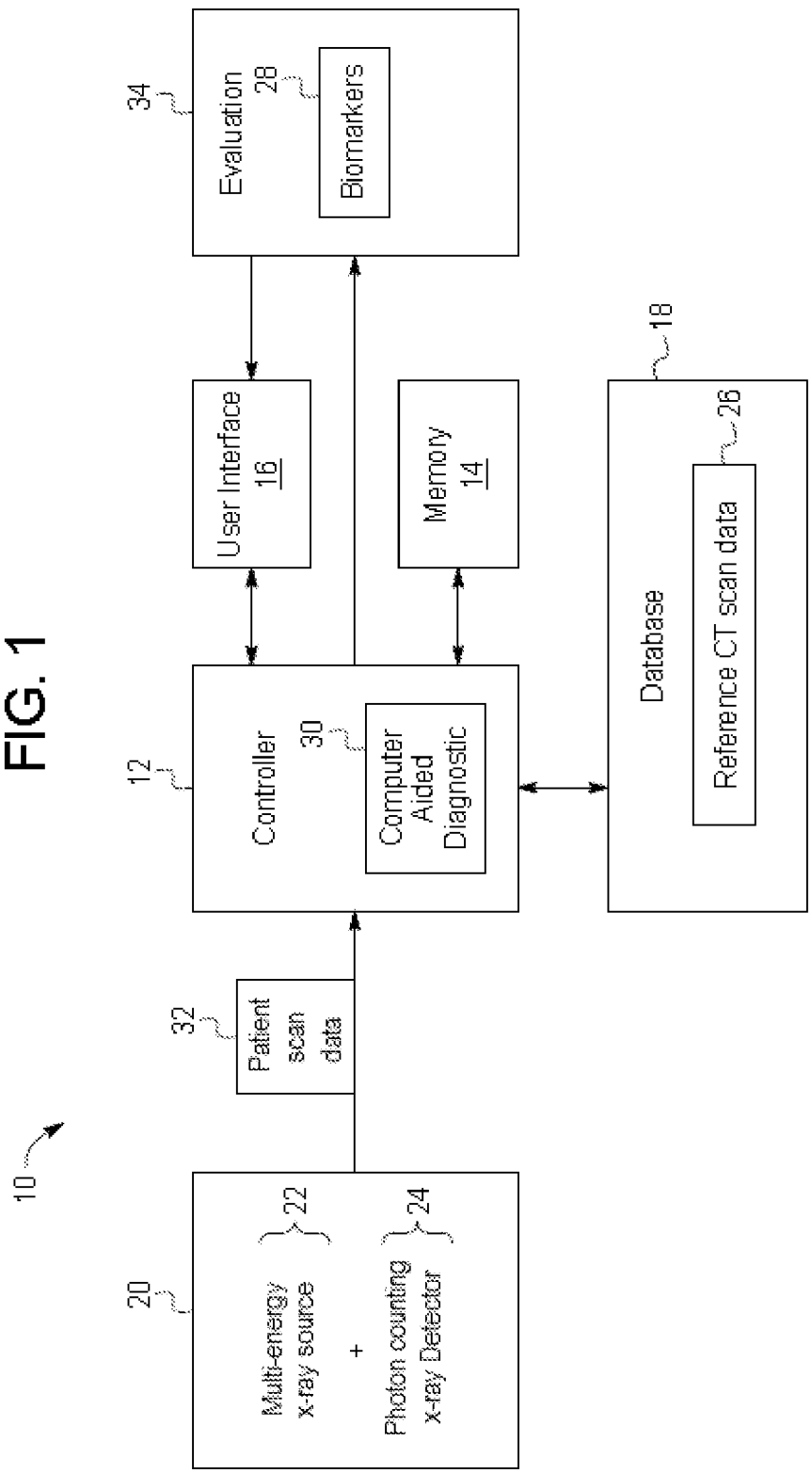
FIG. 1 is a schematic of an embodiment of the system disclosed herein.

The following description details embodiments of inventive systems and methods for evaluating a brain scan using reference data. The systems and methods use a dataset provided from a medical imagining device to derive an objective diagnosis of concussions or mTBI. The examples below rely primarily on the example of using a CT scanner as the medical imagining device, but it is understood that the advantages of the systems and methods provided herein can be attained using alternative, or additional, medical imaging devices.

FIG. 1 illustrates an example of the present subject matter using a computed tomography system 10. As shown in FIG. 1, the computed tomography system 10 includes a CT scanner 20 including a multi-energy x-ray source 22 in connection with a photon counting x-ray detector 24 configured to collect a patient scan data 32 of a patient.

The CT scanner 20 uses a rotating anode (x-ray source 22) to generate x-rays that pass through an object and are collected on the other side with a photon counting x-ray detector 24. The signal detected reflects the intensity of the x-ray after "attenuation" through the object (patient). The computed tomography system 10 may use computer algorithms to reconstruct and display observable images of cross sections from three-dimensional x-ray datasets (the raw data set is a "sinogram").

Specifically, the CT scanner 20 includes a multi-energy x-ray source 22 to define the absolute and relative values of brain constituents uncovered by spectral decomposition for comparison of healthy and post-concussive impact x-ray scan data. CT scanner 20 ("spectral CT" or "spectroscopic CT") uses a multi-energy x-ray source 22 that applies x-rays at different kVp levels during a single scan, which enables the identification and quantification of the constituent elements of brain tissue and the cranium based on their relative energy spectra.

X-ray attenuation is measured in "Hounsfield Units" (HU). Materials with the same HU at one energy level have different HU at another. The difference in HU between energies is characteristic of the material (in other words, the atomic number and electron density of a selected volume of tissue can be determined based on the spectral properties of that tissue). The ability to differentiate tissues is dependent upon their relative spectral attenuation.

The photon-counting x-ray detector 24 maximizes the accuracy of x-ray attenuation comparisons, decreases x-ray scatter and noise, and minimizes effective radiation dose. Conventional CT is ineffective in diagnosing the subtle changes in brain tissue that occur following mTBI because the images of linear attenuation coefficients are not tissue-type specific, the contrast between different tissues is not sufficient, and potentially harmful x-ray radiation dose must be increased (by kVp and/or repeated scans) to optimize image quality to maximize the possibility of visually detecting subtle changes in tissue.

The present computed tomography system 10 includes a photon counting x-ray detector (PCXD) 24 with energy discrimination capabilities (from the multi-energy x-ray source 22) that may potentially eliminate the limitations associated with conventional CT scans. The computed tomography system 10 may use the multi-energy x-ray source 22 to recognize calcium based cranium and the computer aided diagnostic 30 algorithm to remove the skull from the patient scan data 32.

The CT scanner 20 is adapted to scan the brain of an individual patient to acquire patient scan data 32 for evaluation. In a preferred embodiment, the CT scanner 20 is capable of acquiring patient scan data 32 including a low-energy scan and a high-energy scan. It is contemplated that the CT scanner 20 may be any kind of CT scanner. Further, it is understood that any number of data acquisition devices and methods could be substituted for the CT scanner 20, such as diffusion tensor imaging, functional magnetic resonance imaging (fMRI), magnetic resonance imaging (MRI), positron emission tomography (PET), etc. Accordingly, the examples used herein may be instructive for other data acquisition devices as will be understood by one of skill in the art. As noted previously, for the purposes of clarity, the examples provided herein focus primarily on the use of a CT scanner 20 for data acquisition.

The CT scanner 20 may be better adapted to scan the brain by incorporating hardware changes. For example, shutter cameras may be added to the CT scanner 20 to enable the CT scanner to pinpoint scan particular areas of the brain to enhance recognition of data that otherwise may be faintly recorded in the patient scan data 32.

The computed tomography system 10 further includes a controller 12 and memory 14 coupled to the controller 12, wherein the memory 14 is configured to store program instructions executable by the controller 12. In response to executing the program instructions, the controller 12 is configured to access the patient scan data 32 from the photon-counting x-ray detector 24.

The controller 12 is configured to access a reference CT scan data 26 associated with the patient from a database 18 in communication with the controller 12, wherein the database 18 includes a plurality of reference CT scan data 26 associated with a plurality of patients. The database 18 may store both the patient specific and non-patient specific reference CT scan data 26. In other words, the reference CT scan data 26 may include patient-specific baseline reference CT scan data 26 or non-patient specific healthy baseline reference CT scan data 26 of a plurality of healthy people. The database 18 may further include standard anatomical measurements (e.g., used in phantoms) used to analyze the patient scan data 32.

For example, the reference CT scan data 26 may include CT scan data of a population of healthy individuals and from individuals known to have brain injuries. Reference CT scan data 26 may also include pre-determined indicators that indicate brain injury. Such reference CT scan data 26 is used to determine a "delta" for the reference CT scan data 26 for key measurements that have been derived from the evaluation of the reference CT scan data 26 population. For example, the reference CT scan data 26 may indicate that identified increases in brain density at a specific location are indicative of brain injury. Accordingly, when comparing patient scan data 32 to reference CT scan data 26, if a significant delta is found for the brain density measurement at that specific location, the system may flag the measurement as potentially identifying brain injury.

In one example wherein the reference CT scan data 26 includes scan data of a population, the population includes individuals known to have brain injury or indicators of brain injury (as determined by an alternative method). In a preferred embodiment, the reference CT scan data 26 of a population includes reference CT scan data 26 of individuals shortly after receiving a concussion. In another preferred embodiment, the reference CT scan data 26 of a population includes individuals known to have chronic traumatic encephalopathy (as may be indicated by levels of tau protein in the brain tissue or otherwise). The reference CT scan data 26 may be assembled and categorized from the population by determining the differences between the individuals known to have brain injury or indicators of brain injury and healthy individuals. Reference CT scan data 26 may include scans of the population at various energy levels. Reference CT scan data 26 may include scans of the same individuals taken over time to draw out the baseline in brains changes over time, in response to treatments, in response to events, etc.

Reference CT scan data 26 may be pre-processed in preparation for the analysis. For example, the reference CT scan data 26 may be pre-processed to derive indicators for inclusion in the reference CT scan data 26, such as thresholds, numerical weights, pre-computed features, etc., that correlate with brain health or brain injury in the population and may be used in performing the analysis between the patient [CT] scan data 32 and the reference CT scan data 26. Additionally, reference CT scan data 26 may be pre-processed to remove irrelevant features, emphasize important features, remove aliasing, remove artifacts, enhance contrast etc. Further, reference CT scan data 26 may be an aggregation of reference CT scan data 26 from multiple individuals or an aggregation of scans from some individuals contributing multiple scans.

As mentioned above, the controller 12 is configured to analyze the patient scan data 32 in comparison to the stored reference CT scan data 26, and display the results of the objective diagnostic evaluation 34 of the patient [CT] scan data 32 on a user interface 16. For example, the controller 12 may analyze the patient scan data 32 and the reference CT scan data 26 using a computer aided diagnostic 30 to identify biomarkers 28 indicating a mild traumatic brain injury and display a diagnosis indicating the presence or lack of mTBI.

The results of the objective diagnostic evaluation 34 of the patient scan data 32 may identify locations in the brain where trauma occurred. The results of the objective diagnostic evaluation 34 of the patient scan data 32 may further be a determination that a concussion has occurred and the degree of injury. Also, the results of the objective diagnostic evaluation 34 of a patient scan data 32 may be a determination that an individual has injury associated with repetitive traumatic brain injury, such as chronic traumatic encephalopathy, or a probabilistic likelihood an individual has such injury.

In a presently preferred embodiment, the analysis of the patient scan data 32 and the reference CT scan data 26 is performed using computer-aided diagnostic (CAD) 30. The CAD 30 incorporates the tissue identification and classification obtained from the spectral decomposition function of the multi-energy x-ray source 22 and, focusing on regions of interest (ROI), can isolate for quantification/quality comparison those brain tissues with certain atomic characteristics and ignore (subtract) other irrelevant tissue from consideration, a "content-aware data-mining function. The CAD 30 may leverage successful data-mining methods, using data directly and/or indirectly representing the appropriate diagnostic conditions to compare and contrast volume measurements mined from the raw data of volumetric CT scans for changes in the size of the cerebral ventricles and water content in cerebral spinal fluid (CSF).

Specifically, the evaluative technique may include identifying various biomarkers 28 that identify brain injury or damage or may be used to assess brain injury or damage. In a preferred embodiment, the evaluation 34 may include a biomarker 28 of the tau protein levels. Alternatively, biomarkers 28 may indicate changes in the brain, such as, tissue consistency or density, size or shape of the brain (swelling), scar tissue, brain matter consistency, neuro-conductivity, blood vessel deterioration, blood vessel build up, tau protein tangles, plaque build up (for example, amyloid plaque), cellular level related changes, etc.

Biomarkers 28 may also include (1) shear and tensile axonal injuries in the corpus callosum, deep WM tracts of both cerebral hemispheres and the brainstem, (2) focal gray matter (GM) and WM atrophy (volume loss), (3) whole brain volumetric atrophy (detected by DTI), (4) edema/neuro-inflammation (by DTI using fractional anisotropy (FA) metrics), (5) WM integrity changes (tract-based spatial statistics, "TBSS" deviation in DTI metrics in comparison between normative sample and post-mTBI DTI scans), (6) hemosiderin (a blood by-product residual from shearing of the microvasculature or breakdown of the vascular wall from trauma), (7) micro-hemorrhages, (8) trauma-related vascular pathology (detected by SWI), and (9) WM hyperintensities (WM abnormality and/or increased perivascular space in the gray/white matter interface or corpus callosum) (detected by FLAIR).

Biomarkers 28 for mTBI may further include: (1) macrophages and hemosiderin in WM (from brain tissue analysis in autopsy), (2) a surge of astrocytic protein S100B, (3) excreted actin-associated proteins "ezrin" and "moesin" (mass spectrometry—cell cultures), and (4) elevated levels of neuronal proteins Neurofilament-Heavy Chain (pNFH). (detected in analysis of CSF), and (5) unusual deposition of beta-amyloid and tau proteins.

Additional biomarkers 28 may include: blood vessel build-up around tau protein tangles, bleeding within the corpus callosum or cerebral cortex, stretching and tearing of brain tissue, compression of brain tissues, tearing of blood vessels, ventricle size, fluid levels within the brain, atrophy of the frontal and temporal cortices, or of the medial temporal lobe of the brain, shifting of intracranial structures, intracranial hematomas, brain hemorrhages, focal lesions/structural lesions, contusions of the brain-blood mixed among tissue, cerebral edema, tissue density, weight of the brain, brain structure and chemistry, blood flow changes, including ischemia, relative content, including content of water, fluid, air, bone, (new) waste product, vacuum (absence) of tissue/matter, osmotic pressure (dilution of tissue), hypotension, displacement of cerebral fluid in ventricles and canals, tau deposition, immunoreactive deposits, neuronal loss, change in location of neuronal activity, projections to the cortex, sub-visual fractures and other damage to the cranium, the size of the brain, intra-cranial pressure, electrical and chemical connections/communications within the brain, the volume of the brain or of specific lobes of the brain.

The computed tomography system 10 is configured to automatically identify and eliminate matching data points between a baseline (healthy) brain CT, such as the reference CT scan data 26, and post-concussive CT in a patient scan data 32, separating the signal from the "big data noise." The computer-aided diagnostic 30 may perform a three-dimensional subtraction function with auto-detection of (surrogate) changes. Alternatively, the computed tomography system 10 can be used to re-scan automatically detected regions of interest (ROI) after set times (e.g., every hour over 12 hours), wherein the changes are diagnostic evidence to be evaluated for a diagnosis of mTBI. The computed tomography system 10 indicates outlier data points, isolated for evaluation by a [computed-aided] computer-aided diagnostic 30 and analysis of raw volumetric datasets between healthy and post-concussed brains.

As noted, the results of the objective diagnostic evaluation 34 of the patient scan data 32 is based on a comparison of the patient scan data 32 and reference CT scan data 26. In one example, the reference CT scan data 26 are baseline scans of the individual being evaluated. Baseline reference CT scan data 26 of the individual may include scans that are taken at previous times. Reference CT scan data 26 may be taken over time to draw out the baseline/norms in brains changes over time, in response to treatments, in response to events, etc. Reference CT scan data 26 may further include scans taken before a potentially concussive event. For example, reference CT scan data 26 may be taken before a football game and a patient scan data 32 may be taken after the game. The reference CT scan data 26 may be compared with the baseline scans of the individual to determine changes that may be known to indicate injury and disease.

In a preferred embodiment, the patient scan data 32 includes a first brain scan performed at a low energy and a second brain scan performed at a high energy, which are respectively compared with a first reference CT scan data 26 performed at a low energy and a second reference CT scan data 26 performed at a high energy. The energy levels for the first patient scan data 32 and the first reference CT scan data 26 may or may not be at the same energy level. Likewise, the energy levels for the second patient scan data 32 and the second reference CT scan data 26 may or may not be at the same energy level.

In further embodiments, the controller 12 may further be in communication with a PET scanner to receive PET scan data. In addition to evaluating the scan data in comparison with the reference scans, the controller 12 may further evaluate the patient scan data 32 in comparison with the PET scan data to identify a position or positions in the brain where trauma occurred.

After evaluation, the patient scan data 32 may be stored in the database 18 for future use as reference CT scan data 26. As discussed above, reference CT scan data 26 may include baseline scans of the individual being evaluated, and reference scans of a population and/or composite scan data. Reference CT scan data 26 may be gathered from and shared with a database accessible to the public so that a crowd-sourced analysis of the reference CT scan data 26 may be used to refine the reference CT scan data 26.

The user interface 16 may be adapted to provide the results of the objective diagnostic evaluation 34 of the patient scan data 32 to a user. In a preferred embodiment, the user interface 16 is a display, such as an LCD display. In further embodiments, the user interface 16 may be adapted to store the results of the objective diagnostic evaluation 34 of the patient scan data 32 in a patient file or patient database 18.

In addition to the results of the objective diagnostic evaluation 34 of the patient scan data 32, the computed tomography system 10 may be adapted to display a visual representation of the patient scan data 32 using indicia to identify the location of the biomarkers 28, i.e., a position or positions in the brain where injury occurred. The indicia may highlight changes in density or pressure relative to reference scans. Further, the indicia may include arrows to identify specific regions of damage or other interest. However, it is primarily understood that the results of the objective diagnostic evaluation 34 of the patient scan data 32 may be displayed as a diagnosis of injury that may or may not include images. The objective diagnostic evaluation 34 of the patient scan data 32 may be displayed to show a probabilistic estimate of the likelihood of injury. For example, based on the comparison of the patient scan data 32 and reference CT scan data 26, a visual representation may be displayed that includes an arrow pointed towards a specific location of the brain and an associated probabilistic estimate of the likelihood of injury of, for example, 92%.

The diagnostic accuracy of computed tomography system 10 to diagnose concussion can be verified by cross-checking its results against DTI and other specialized MR neuroimaging techniques used in detecting biomarkers for mTBI, PET with the UCLA proprietary radioisotope used to successfully image tau protein deposition in living patients to diagnose CTE, and microscopic tissue analysis. As in many CAD 30 techniques, if a subset of potential biomarkers 28 are identified through the computed tomography system 10, human judgment may be applied to evaluate the subset of outlier changes in the brain.

FIG. 2 shows as example of a method of diagnosing mTBI (method 11). As shown in FIG. 2, the method 11 includes a first step 36 of acquiring patient scan data 32. As described above, the patient scan data 32 may be acquired through a medical imaging device, such as a CT scanner 20, or other medical imaging device, such as an MRI device, a PET device, etc.

In a second step 38, reference CT scan data 26 is accessed. This reference CT scan data 26 may be from earlier scans of the current patient, other patients, aggregated data, etc. A third step 40 includes analyzing the patient scan data 32 and the one or more sets of reference CT scan data 26. In a preferred embodiment, the analysis is performed using a computer-aided diagnostic 30 looking for biomarkers 28 indicative of a diagnosis of mTBI. The computer-aided diagnostic 30 may include a three-dimensional subtraction algorithm between the patient scan data 32 and the reference CT scan data 26 to identify differences to indicate one or more biomarkers 28.

A fourth step 42 includes generating an evaluation indicative of a diagnosis of mTBI. The evaluation is the analytic result of the analysis performed in the third step 40.

A fifth step 44 includes displaying the results of the evaluation on a user interface 16. The evaluation may be displayed, for example, on a user interface 16 of a medical imaging device, a personal computer, mobile device, etc.

As described above, aspects of the systems and methods described herein are controlled by one or more controllers 12. The one or more controllers 12 may be adapted to run a variety of application programs, access and store data, including accessing and storing data in the associated databases 18, and enable one or more interactions as described herein. Typically, the controller 12 is implemented by one or more programmable data processing devices. The hardware elements, operating systems, and programming languages of such devices are conventional in nature, and it is presumed that those skilled in the art are adequately familiar therewith.

For example, the one or more controllers 12 may be a PC based implementation of a central control processing system utilizing a central processing unit (CPU), memory 14 and an interconnect bus. The CPU may contain a single microprocessor, or it may contain a plurality of microprocessors for configuring the CPU as a multi-processor system. The memory 14 may include a main memory, such as a dynamic random access memory (DRAM) and cache, as well as a read only memory, such as a PROM, EPROM, FLASH-EPROM, or the like. The system may also include any form of volatile or non-volatile memory 14. In operation, the memory 14 stores at least portions of instructions for execution by the CPU and data for processing in accord with the executed instructions.

The one or more controllers 12 may also include one or more input/output interfaces 16 for communications with one or more processing systems. Although not shown, one or more such interfaces 16 may enable communications via a network, e.g., to enable sending and receiving instructions electronically. The communication links may be wired or wireless.

The one or more controllers 12 may further include appropriate input/output ports for interconnection with one or more output mechanisms (e.g., monitors, printers, touchscreens, motion-sensing input devices, etc.) and one or more input mechanisms (e.g., keyboards, mice, voice, touchscreens, bioelectric devices, magnetic readers, RFID readers, barcode readers, motion-sensing input devices, etc.) serving as one or more user interfaces for the controller 12. For example, the one or more controllers 12 may include a graphics subsystem to drive the output mechanism. The links of the peripherals to the system may be wired connections or use wireless communications.

Although summarized above as a PC-type implementation, those skilled in the art will recognize that the one or more controllers 12 also encompasses systems such as host computers, servers, workstations, network terminals, and the like. Further one or more controllers 12 may be embodied in a device, such as a mobile electronic device, like a smartphone or tablet computer. In fact, the use of the term controller 12 is intended to represent a broad category of components that are well known in the art. Even further, the controllers 12 may be embodied in one or more medical imaging devices.

Hence aspects of the systems and methods provided herein encompass hardware and software for controlling the relevant functions. Software may take the form of code or executable instructions for causing a controller 12 or other programmable equipment to perform the relevant steps, where the code or instructions are carried by or otherwise embodied in a medium readable by the controller 12 or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as the memory 14 of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, any other memory chip or cartridge, or any other medium from which a controller 12 can read programming code and/or data. Many of these forms of computer readable media may be involved in carrying one or more sequences of one or more instructions to a processor for execution.

It should be noted that various changes and modifications to the embodiments described herein will be apparent to those skilled in the art. Such changes and modifications may be made without departing from the spirit and scope of the present invention and without diminishing its attendant advantages. For example, various embodiments of the method and portable electronic device may be provided based on various combinations of the features and functions from the subject matter provided herein.

I claim:

1. A system for diagnosing mTBI comprising:
 a medical imaging device configured to collect a patient scan data related to a patient's brain;
 a controller;
 a memory coupled to the controller, wherein the memory is configured to store program instructions executable by the controller;
 a database in communication with the controller; and
 a computer aided diagnostic in communication with the controller;
 wherein in response to executing the program instructions, the controller is configured to:
  access the patient scan data;
  access reference scan data from the database, wherein the reference scan data provides one or more sets of baseline reference scan data; and
  analyze the patient scan data and the one or more sets of baseline reference scan data using the computer aided diagnostic to provide an objective indication of whether a mild traumatic brain injury is present in the patient scan data, wherein the objective indication is provided as an output that is distinct from a visual representation of the patient scan data.

2. The system of claim 1, wherein the medical imaging device comprises a multi-energy x-ray source and a photon counting detector.

3. The system of claim 1, further comprising a user interface wherein the controller is further configured to display the objective indication on the user interface.

4. The system of claim 1, wherein the computer-aided diagnostic includes a three-dimensional subtraction algorithm between the patient scan data and the reference scan data to identify differences to indicate one or more biomarkers.

5. The system of claim 4, wherein the one or more biomarkers are selected from the group consisting of: blood vessel build-up around a tau protein tangle, bleeding within the corpus callosum, bleeding within the cerebral cortex, stretching of brain tissue, tearing of brain tissue, compression of brain tissue, tearing of blood vessels, change in ventricle size, and change in brain fluid levels.

6. The system of claim 4, wherein the one or more biomarkers may be are selected from the group consisting of: atrophy of frontal cortex, atrophy of temporal cortex, atrophy of the medial temporal lobe, shifting of intracranial structures, intracranial hematomas, brain hemorrhages, lesions, contusions, cerebral edema.

7. The system of claim 4, wherein the one or more biomarkers are selected from the group consisting of: tissue density, changes in blood flow, ischemia, change in fluid levels, absence of tissue, osmotic pressure, hypotension, tau deposition, immunoreactive deposits, neuronal loss, and sub-visual fractures in the cranium.

8. The system of claim 4, wherein the one or more biomarkers are selected from the group consisting of: blood vessel build-up around tau protein tangles, bleeding within the corpus callosum or cerebral cortex, stretching and tearing of brain tissue, compression of brain tissues, tearing of blood vessels, ventricle size, fluid levels within the brain, atrophy of the frontal and temporal cortices, or of the medial temporal lobe of the brain, shifting of intracranial structures, intracranial hematomas, brain hemorrhages, focal lesions/structural lesions, contusions of the brain-blood mixed among tissue, cerebral edema, tissue density, weight of the brain, brain structure and chemistry, blood flow changes, including ischemia, relative content, including content of water, fluid, air, bone, (new) waste product, vacuum (absence) of tissue/matter, osmotic pressure (dilution of tissue), hypotension, displacement of cerebral fluid in ventricles and canals, tau deposition, immunoreactive deposits, neuronal loss, change in location of neuronal activity, projections to the cortex, sub-visual fractures and other damage to the cranium, the size of the brain, intra-cranial pressure, electrical and chemical connections/communications within the brain, the volume of the brain or of specific lobes of the brain.

9. A method of identifying mild traumatic brain injuries comprising:
acquiring patient scan data of a patient's brain from a medical imaging device;
accessing one or more sets of reference scan data from a database storing a plurality of reference scan data;
analyzing the patient scan data and the one or more sets of reference scan data using a computer aided diagnostic;
generating an evaluation based on the analyzing step, wherein the evaluation diagnoses an indication of a mild traumatic brain injury; and
displaying results of the evaluation on a user interface, wherein an objective indication is provided as an output that is distinct from a visual representation of the patient scan data.

10. The method of claim 9, wherein the medical imaging device comprises a multi-energy x-ray source and a photon counting detector.

11. The method of claim 9, further including acquiring a first patient scan data at a first time and a second patient scan data at a second time, wherein the first patient scan data is stored in the database as the reference scan data.

12. The method of claim 9, wherein the analyzing step includes applying a three-dimensional subtraction algorithm between the patient scan data and the reference scan data to identify differences to indicate one or more biomarkers.

13. The method of claim 12, wherein the one or more biomarkers are selected from the group consisting of: blood vessel build-up around a tau protein tangle, bleeding within the corpus callosum, bleeding within the cerebral cortex, stretching of brain tissue, tearing of brain tissue, compression of brain tissue, tearing of blood vessels, change in ventricle size, and change in brain fluid levels.

14. The method of claim 12, wherein the one or more biomarkers are selected from the group consisting of: atrophy of frontal cortex, atrophy of temporal cortex, atrophy of the medial temporal lobe, shifting of intracranial structures, intracranial hematomas, brain hemorrhages, lesions, contusions, cerebral edema.

15. The method of claim 12, wherein the one or more biomarkers are selected from the group consisting of: tissue density, changes in blood flow, ischemia, change in fluid levels, absence of tissue, osmotic pressure, hypotension, tau deposition, immunoreactive deposits, neuronal loss, and sub-visual fractures in the cranium.

16. The method of claim 12, wherein the one or more biomarkers are selected from the group consisting of: blood vessel build-up around tau protein tangles, bleeding within the corpus callosum or cerebral cortex, stretching and tearing of brain tissue, compression of brain tissues, tearing of blood vessels, ventricle size, fluid levels within the brain, atrophy of the frontal and temporal cortices, or of the medial temporal lobe of the brain, shifting of intracranial structures, intracranial hematomas, brain hemorrhages, focal lesions/structural lesions, contusions of the brain-blood mixed among tissue, cerebral edema, tissue density, weight of the brain, brain structure and chemistry, blood flow changes, including ischemia, relative content, including content of water, fluid, air, bone, (new) waste product, vacuum (absence) of tissue/matter, osmotic pressure (dilution of tissue), hypotension, displacement of cerebral fluid in ventricles and canals, tau deposition, immunoreactive deposits, neuronal loss, change in location of neuronal activity, projections to the cortex, sub-visual fractures and other damage to the cranium, the size of the brain, intra-cranial pressure, electrical and chemical connections/communications within the brain, the volume of the brain or of specific lobes of the brain.

* * * * *